United States Patent [19]
Divone, Sr. et al.

[11] Patent Number: 5,854,336
[45] Date of Patent: Dec. 29, 1998

[54] PROCESS FOR PREPARING SILICONE ELASTOMER COMPOSITIONS

[75] Inventors: Peter Anthony Divone, Sr., New York, N.Y.; Brian John Dobkowski, Shelton, Conn.; Michael Charles Cheney, Fairfield, Conn.; Salvador Pliego, Hamden, Conn.; Walter Anthony Biercevicz, Prospect, Conn.; Kenneth Paul Manzari, West Haven, Conn.

[73] Assignee: Chesebrough-Pond's USA Co., Division of Conopco, Inc., Greenwich, Conn.

[21] Appl. No.: 822,406

[22] Filed: Mar. 20, 1997

[51] Int. Cl.[6] ............... C08J 3/00; C08K 3/20; C08K 7/16; C08L 83/00
[52] U.S. Cl. ............ 524/588; 523/223; 523/318; 524/267; 528/502 C; 528/502 F; 528/15
[58] Field of Search .......... 528/502 C, 502 F, 528/15; 524/267, 588; 523/223, 318

[56] References Cited

U.S. PATENT DOCUMENTS

| | | | |
|---|---|---|---|
| 3,926,413 | 12/1975 | D'Urso | 259/4 R |
| 4,675,194 | 6/1987 | Gaffney | 426/39 |
| 4,720,353 | 1/1988 | Bell | 252/309 |
| 4,742,142 | 5/1988 | Shimizu et al. | 528/15 |
| 4,980,167 | 12/1990 | Harashima et al. | 424/401 |
| 4,983,418 | 1/1991 | Murphy et al. | 424/47 |
| 4,987,169 | 1/1991 | Kuwata et al. | 524/267 |
| 5,006,349 | 4/1991 | Dahlstrom et al. | 426/39 |
| 5,143,722 | 9/1992 | Hollenberg et al. | 424/63 |
| 5,266,321 | 11/1993 | Shukuzaki et al. | 424/401 |
| 5,280,019 | 1/1994 | Klimisch | 514/63 |
| 5,387,417 | 2/1995 | Rentsch | 424/401 |
| 5,654,362 | 8/1997 | Schulz, Jr. et al. | 524/862 |

FOREIGN PATENT DOCUMENTS

| | | |
|---|---|---|
| WO 96/018374 | 6/1996 | WIPO . |
| 97/44010 | 11/1997 | WIPO . |

OTHER PUBLICATIONS

GE Silicones Material Safety Data Sheet Jul. 24, 1996.

*Primary Examiner*—Patrick D. Niland
*Attorney, Agent, or Firm*—Milton L. Honig

[57] ABSTRACT

A process is provided for preparing a silicone elastomer composition for cosmetic products which includes the steps of feeding the silicone elastomer composition comprising a silicone rubber in a carrier fluid into a reactor, mixing the composition in the reactor, delivering the composition from the reactor into a high pressure pump, pumping the fluid into a device for reducing particles of rubber into smaller sizes and recirculating the resultant size reduced particles back to the reactor. The device for reducing particle size is preferably a high pressure fed homogenizer, most advantageously a sonolator.

12 Claims, 1 Drawing Sheet

PROCESS FOR PREPARING SILICONE ELASTOMER COMPOSITIONS

BACKGROUND OF THE INVENTION

1. Field of the Invention

The invention concerns a process for preparing cosmetic products or work-in-progress components of such products which include silicone elastomers as a functional ingredient.

2. The Related Art

Over the last four decades a rich variety of silicone materials have been commercialized for use in cosmetics. Although expensive, silicones have many unusual properties rendering them almost indispensable for certain types of products. Lubricity, compatibility, stability, dispersibility, thickening ability and other properties have been deemed quite valuable.

Among the multitude of silicone materials, the rubber-like polysiloxane elastomers have received attention as components in both aqueous emulsions and non-aqueous formulations. Illustrative of the art is WO 96/18374 (Estee Lauder) describing a stable water-in-oil emulsion incorporating an organopolysiloxane elastomer having a degree of cross-linking sufficient to provide a rubber-like material. A skin treatment cream was exemplified employing Gransil, a mixture of octamethylcyclotetrasiloxane and organopolysiloxane rubber. The components were formulated as three phases which were homogenized with a Silverson Homogenizer. In a second example, a cosmetic foundation was prepared through a combination of low and high shear mixing.

U.S. Pat. No. 4,983,418 (Murphy et al.) discloses hair spray compositions which include a silicone gum which when applied to hair imparts style, retention and conditioning benefits. Diphenyl-dimethyl polysiloxane gum is reported to be the preferred embodiment.

U.S. Pat. No. 5,266,321 (Shukuzaki et al.) describes oily make-up cosmetic compositions normally in solid form. These compositions contain a silicone gel which includes a partially crosslinked organopolysiloxane polymeric compound and a low viscosity silicone oil. The polymeric compound is preferably prepared by the addition polymerization of an organo-hydrogen polysiloxane and an organopolysiloxane having unsaturated aliphatic groups. Solid foundations described in the examples are prepared in a step including homogenization in a triple roll mill.

U.S. Pat. No. 4,980,167 (Harashima et al.) reports cosmetic compositions exhibiting lubricancy derived from a silicone rubber powder ingredient within a silicone oil. A preferred rubber derives from the addition reaction between an organopolysiloxane containing at least two vinyl groups, an organopolysiloxane containing at least two silicon bonded hydrogen atoms and a platinum catalyst. Oily foundations, lipsticks and moisturizing creams are exemplified. Related silicone rubbers are reported in U.S. Pat. No. 4,742,142 (Shimizu et al.). This patent focuses upon synthesis of the rubber.

Although of great potential, the silicone elastomer materials commercially available or even hitherto reported in the literature have physical properties insufficiently suitable for elegant cosmetic products.

Accordingly, it is an object of the present invention to provide a process for preparation of silicone elastomer compositions containing a silicone elastomer within a carrier fluid, the process converting the elastomer to a form stably dispersed in the carrier fluid and exhibiting a silky skinfeel when combined into cosmetic products.

These and other objects of the present invention will become more apparent from the following summary and description.

SUMMARY OF THE INVENTION

A process is provided for preparing silicone elastomer compositions for use in cosmetic products which compositions comprise a silicone elastomer within a carrier fluid, the process including the steps of:

(i) feeding the silicone elastomer composition into a reactor;

(ii) mixing the silicone elastomer composition through agitation in the reactor;

(iii) transferring the agitated silicone elastomer composition from the reactor into a high pressure pump;

(iv) pumping the agitated silicone elastomer composition from the high pressure pump into a device for reducing the silicone elastomer within the composition into a smaller particle size; and (v) optionally, recirculating the resultant smaller sized silicone elastomer particles into the reactor.

The process of this invention is not directed at synthesis of any silicone elastomer but rather concerns a method to physically manipulate a pre-synthesized elastomer into a form more suitable for certain cosmetic products. Transformations of the present invention are intended to customize elastomer particle sizes and composition viscosities to match requirements for the cosmetic product.

The silicone elastomer of the present invention is preferably a crosslinked non-emulsifying siloxane elastomer formed from a divinyl monomer reacting with Si-H linkages of a siloxane backbone. A volatile siloxane such as cyclomethicones are the preferred carrier for delivery of the elastomer through the recirculating system.

The device for reducing particles may be a special variety of homogenizer wherein under pressure the silicone composition is forced through a small orifice with high local energy applied to breakdown particle structure of the silicone elastomer. A particularly preferred device is a sonolator operating with an ultrasonic blade which generates turbulent cavitation bursts.

BRIEF DESCRIPTION OF THE DRAWING

An improved understanding of the invention will be gained from review of FIG. 1 which is a process schematic of a preferred embodiment according to the present invention.

DETAILED DESCRIPTION OF THE INVENTION

Figure 1:
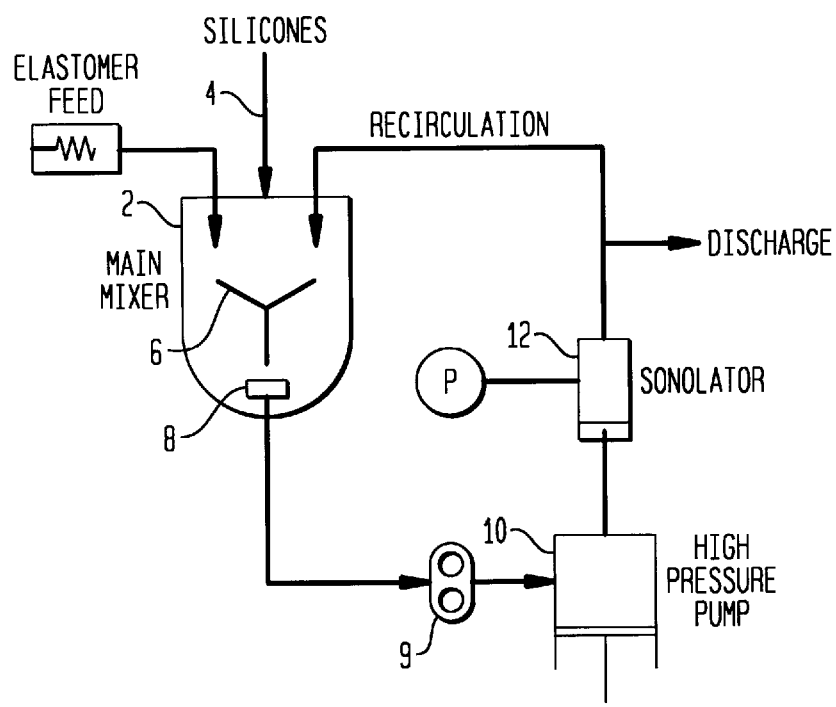

Now it has been discovered that silicone elastomers can be prepared for use with cosmetic products in a procedure which reduces their particle size by repeated treatment in a high pressure fed homogenizer. FIG. 1 illustrates a preferred embodiment. Therein a silicone elastomer dispersed within cyclomethicone at a rubber concentration of from 1 to 100%, preferably from 5 to 30%, optimally from 15 to 20%, is charged to a reactor 2 as a silicone elastomer composition. Additional cyclomethicone carrier in an amount from 0 to 95%, preferably from 50 to 80%, optimally from 65 to 75% by weight based on the amount of final recirculated elastomer composition may be charged to the reactor through a separate feed line 4. The silicone elastomer composition and any additional cyclomethicone carrier is then mixed by a slow speed counter-sweep mixer 6 to agitate the mixture.

Within reactor 2, is a high-shear homogenizer 8 employing a series of blades to produce high energy shear forces onto the mixture. Homogenizer 8 improves the resultant product but is not a necessary element of the process. In some configurations, homogenizer 8 may be placed outside reactor 2 in a location prior to the high pressure pump 10.

Upon completion of agitation in reactor 2, the resultant fluid mixture is delivered from the reactor into a feed pump 9. The feed pump 9 is a positive displacement pump such as Waukesha PD gear pump. Thereafter the fluid mixture is transferred to a high pressure pump 10. Pressures generated by pump 10 may range from 500 to 40,000, preferably from 1,200 to 20,000, optimally from 1,800 to 10,000 psi. Typically, pump 10 may be a triplex plunger type available from the Giant Corporation, Toledo, Ohio or from the Cat Corporation.

Silicone elastomer composition under high pressure is then pumped into a type of homogenizer 12 requiring fluid to pass through a narrow orifice which reduces particle size. The preferred embodiment employs a sonolator available from the Sonic Corp., a unit of General Signal. The sonolator is an in-line device capable of converting the kinetic energy of a high velocity stream of liquid into a high intensity mixing action. Conversion is accomplished by pumping the liquid through an orifice against a bladelike obstacle immediately in the jet stream of the liquid. The liquid itself oscillates in a stable vortexing pattern, which in turn causes the blade-like obstacle to resonate, resulting in a high level of cavitation, turbulence and shear. The blade or knife is brought into an ultrasonic vibration by the fluid motion, which causes cavitation in the fluid. The cavitation (a phenomenon in which small gas bubbles in the fluid start to grow until they implode with very high local energy dissipation rates) then breaks up the droplet particles. U.S. Pat. No. 3,176,964 to Cottell et al. describes the sonolator in detail and its disclosure is hereby incorporated by reference.

Alternative high-pressure fed homogenizers other than the sonolator (preferred) are the Manton Gaulin type homogenizer available from the APV Manton Corporation and the Microfluidizer available from Microfluidics Corporation. These type high pressure homogenizers contain a valve which is pressed (hydraulically or by a spring) against a fixed valve seat. Under high pressure, fluid flows through the opening in the seat and then through a gap between the valve and seat. Although geometries of different high pressure homogenizers may differ in details, and may even be roughened with sharp edges, they all are generally similar. Often the high pressure homogenizer may consist of two or more valve-seat combinations.

Subsequent to high pressure homogenization, the silicone elastomer composition may, for best results, be recirculated into reactor 2. Recirculation according to the present process normally ranges from 1 to 200 passes, preferably from 2 to 60 passes, optimally from 10 to 40 recycling passes. Temperatures within reactor 2 and throughout the system may range from 20° to 100° C., preferably from 35° to 60° C., optimally from 50° to 70° C. Silicone rubber particles resulting from the process will have an average particle size ranging from 0.05 to 30 micron, preferably from 0.2 to 10 micron, optimally from 0.5 to 5 micron. These particles are uniformly dispersed within the silicone oil (e.g. cyclomethicone) carrier.

Silicone elastomers of the present invention preferably are crosslinked non-emulsifying siloxane elastomers with average number molecular weights in excess of 10,000, preferably in excess of 1 million and optimally will range from 10,000 to 20 million. The term "non-emulsifying" defines a siloxane from which polyoxyalkylene units are absent. Advantageously the rubbers are formed from a divinyl monomer reacting with Si-H linkages of a siloxane backbone. Elastomer compositions are commercially available from the General Electric Company under product designation General Electric Silicone 1229 named Polydimethyl-HydrogenSiloxane -Reaction Products with Vinyl Terminated Polydimethylsiloxane, delivered as 20–35% rubber in a cyclomethicone carrier. A related elastomer under the CTFA name of Crosslinked Stearyl Methyl Dimethyl Siloxane Copolymer is available as Gransil SR-CYC (25–35% active elastomer in cyclomethicone) from Grant Industries, Inc., Elmwood Park, N.J.

Amounts of the elastomer dispersed in the final cosmetic product formulated with the elastomeric composition derived from the process may range from 0.1 to 50%, optimally from 1 to 40%, most preferably from 3 to 20% by weight.

Carriers for the silicone elastomer may principally be silicone fluids. Illustrative of this category are the cyclo polydimethyl siloxane fluids of the formula $[(CH_3)_2SiO)]_x$, wherein x denotes an integer of from 3 to 6. The cyclic siloxanes will have a boiling point of less than 250° C. and a viscosity at 25° C. of less than 10 centipoise. Cyclomethicone is the common name of such materials. The tetramer and pentamer cyclomethicones are commercially available as DC 244 or 344 and DC 245 or 345 from the Dow Corning Corporation. Also useful is hexamethyldisiloxane available as DC 200 fluid (0.65 cs).

Hydrophobic carriers other than silicone fluids may also be employed as carriers. Petrolatum is the most preferred. Other hydrocarbons that may be employed include mineral oil, polyolefins such as polydecene, and paraffins such as isohexadecane (e.g. Permethyl 99® and Permethyl 101®).

Compositions subject to the present method may either be anhydrous or contain water. When anhydrous, the amount of water will be confined to range from 0 to 5%, preferably not above 2%, optimally not above 0.5% by weight. When the compositions of this invention are in emulsion form, the amount of water will range from 5 to 50%, preferably from 7 to 30%, optimally from 10 to 20% by weight. The emulsions may be of the oil-in-water, water-in-oil or duplex variety. Aqueous to oily phases can range in weight from 10:1 to 1:10, preferably from 1:1 to 1:5, optimally from 1:1 to 1:2.

Hydrophillic carriers other than water may be present such as polyhydric alcohols. Typical polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, glycerin, ethoxylated glycerin, propoxylated glycerin and mixtures thereof. Most preferably the alcohol is glycerin. Amounts of alcohol may range anywhere from 1 to 50%, preferably from 10 to 40%, optimally from 25 to 35% by weight of the cosmetic product.

Beyond the basic components, other materials may be included depending upon the particular type of cosmetic composition sought. For instance, surfactants may be formulated into the compositions. These may be selected from nonionic, anionic, cationic or amphoteric emulsifying agents. They may range in amount anywhere from about 0.1 to about 20% by weight. Illustrative nonionic surfactants are alkoxylated compounds based on $C_{10}$–$C_{22}$ fatty alcohols and acids, and sorbitan. These materials are available, for instance, from the Shell Chemical Company under the Neodol trademark. Copolymers of polyoxypropylene-polyoxyethylene, sold by the BASF Corporation under the Pluronic trademark, are sometimes also useful. Alkyl polyglycosides available from the Henkel Corporation may also be utilized for purposes of this invention.

Anionic type surfactants include fatty acid soaps, sodium lauryl sulphate, sodium lauryl ether sulphate, sodium or magnesium glyceryl ether sulphonates, alkyl benzene sulphonate, mono- and di-alkyl acid phosphates and sodium fatty acyl isethionate.

Amphoteric surfactants include such materials as dialkylamine oxide and various types of betaines (such as cocoamidopropyl betaine).

Preservatives can desirably be incorporated into the elastomer and cosmetic compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable traditional preservatives are hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methyl paraben, propyl paraben, imidazolidinyl urea, sodium dehydroxyacetate and benzyl alcohol. The preservatives should be selected having regard for the use of the composition and possible incompatibilities between the preservatives and other ingredients. Preservatives are preferably employed in amounts ranging from 0.01% to 2% by weight of the composition.

Minor adjunct ingredients may also be included such as fragrances, antifoam agents, opacifiers and colorants, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

This Example illustrates processing of a silicone elastomer composition into a work-in-progress constituent of a water-in-oil skin lotion. A 25 gallon reactor fitted in an upper area with a low shear counter-sweep mixing blade and in a lower area with a homogenizing blade was charged with the components listed in Table I.

TABLE I

| Silicone Elastomer Composition | |
|---|---|
| COMPONENTS | WEIGHT % |
| General Electric Elastomer 1229 (25% rubber solids in cyclomethicone) | 25 |
| Dow Corning 345 (cyclomethicone pentamer) | 45 |
| Dow Corning 244 (cyclomethicone tetramer) | 30 |

Temperatures throughout the process were maintained between 17° and 28° C. Under pressure the fluid blend of Table I was fed to a sonolator operating between 246 and 295 rpm maintaining a pressure between 2,800 and 3,500 psi. Sonolated product was then returned to the reactor. A total of 19 passes recirculated fluid blend through the system. Resultant silicone elastomer composition exhibited a viscosity of 560 cps at 25° C. with elastomer of particle size sufficiently small and dispersed within the cyclomethicone carrier to avoid any grainy feel. Viscosity measurements were taken on a Brookfield LV Viscometer (size 4 bar, 60 rpm, 15 sec.). Broad range of acceptable viscosity can vary from 500 to 40,000 cps at 25° C.

EXAMPLE 2

An essentially anhydrous final cosmetic product was prepared utilizing a silicone elastomer composition. The formulas are shown in Table II.

TABLE II

| COMPONENT | SILICONE ELASTOMER COMPOSITION (WEIGHT %) | FINAL COSMETIC PRODUCT (WEIGHT %) |
|---|---|---|
| General Electric Elastomer 1229 (34% elastomer solid in cyclomethicone) | 33.5 | 31.0 |
| Dow Corning 345 (cyclomethicone pentamer) | 45.4 | 42.0 |
| Dow Corning 344 (cyclomethicone tetramer) | 9.2 | 8.5 |
| Petrolatum (2.5 Hard) | 11.9 | 11.0 |
| Potassium Lactate (50% aqueous soln.) | 0.0 | 7.0 |
| Abil EM 90 (cetyl dimethicone copolyol) | 0.0 | 0.5 |

A 25 gallon reactor was charged with the silicone elastomer composition listed in Table II. Contents of the reactor were agitated with a Press-Industria mixer for a period of several minutes. A 25 DO Waukesha pump transferred the composition from the reactor to a high pressure pump operating at approximately 1,200 psi and thereafter into a sonolator (74–120 rpm). Sonolated fluid was then returned to the reactor and recycled through the system at flow rates ranging from 9 to 34 pounds per minute. Total process time was 3 hours. The system was maintained at a temperature 54° to 62° F.

Sonolated fluid composition resulting from the process had a viscosity between 40,000 and 125,000 cps at 25° C. measured on a Brookfield RTD (5 rpm heliopath spindle −30 sec). The composition was then combined with potassium lactate (50% solution) and a silicone copolyol (Abil EM 90) by agitation at a temperature between 37° to 60° F. The final cosmetic product formulation is listed in Table II.

Although the present invention has been described with reference to preferred embodiments, those skilled in the art will recognize that modifications can be performed without departing from the spirit and purview of the present invention.

What is claimed is:

1. A process for preparing silicone elastomer compositions for use in cosmetic products which compositions comprise a silicone elastomer within a carrier fluid, the process comprising the steps of:

(i) feeding the silicone elastomer composition into a reactor;

(ii) mixing the silicone elastomer composition through agitation in the reactor;

(iii) transferring the agitated silicone elastomer composition from the reactor into a high pressure pump;

(iv) pumping the mixed silicone elastomer composition at a pressure ranging from 500 to 40,000 psi from the high pressure pump into a means for reducing the silicone elastomer within the composition into a smaller particle size;

(v) optionally, recirculating the resultant smaller sized silicone elastomer particles into the reactor; and (vi) recovering a silicone elastomer composition wherein the silicone elastomer average particle size ranges from 0.05 to 30 micron.

2. The process according to claim 1 wherein pumping is performed at a pressure from 1,800 to 10,000 psi.

3. The process according to claim 1 wherein temperature ranges from 20° to 100° C.

4. The process according to claim 1 wherein recirculating between step (ii) and (v) ranges from 1 to 200 passes.

5. The process according to claim 1 wherein the means is a homogenizer.

6. The process according to claim 5 wherein the homogenizer is a device capable of converting kinetic energy of a high velocity stream of liquid into a high intensity mixing action, conversion being accomplished by pumping the liquid through an orifice against a bladelike obstacle immediately in the stream of the liquid.

7. The process according to claim 1 wherein the silicone elastomer is dispersed within a silicone carrier.

8. The process according to claim 1 wherein the average particle size ranges from 0.5 to 5 micron.

9. The process according to claim 1 wherein the silicone elastomer is a crosslinked non-emulsifying polysiloxane prepared from the reaction of a vinyl monomer and a Si—H siloxane.

10. The process according to claim 1 wherein the carrier fluid is cyclomethicone.

11. The process according to claim 1 further comprising applying high-shear force onto the mixed silicone elastomer composition subsequent to step (ii) but prior to step (iv).

12. The process according to claim 1 wherein the transferring step (iii) is with a positive displacement pump.

* * * * *